(12) United States Patent
Petito

(10) Patent No.: US 10,487,824 B2
(45) Date of Patent: Nov. 26, 2019

(54) METHOD OF MAKING A HYDROLYZED COLLAGEN GEL

(71) Applicant: George D. Petito, Bethlehem, PA (US)

(72) Inventor: George D. Petito, Bethlehem, PA (US)

( * ) Notice: Subject to any disclaimer, the term of this patent is extended or adjusted under 35 U.S.C. 154(b) by 337 days.

(21) Appl. No.: 15/393,098

(22) Filed: Dec. 28, 2016

(65) Prior Publication Data
US 2018/0179249 A1    Jun. 28, 2018

(51) Int. Cl.
| | | |
|---|---|---|
| *C07K 14/78* | (2006.01) | |
| *A61K 38/01* | (2006.01) | |
| *A61K 45/06* | (2006.01) | |
| *A61K 8/65* | (2006.01) | |
| *A61K 8/04* | (2006.01) | |
| *F04B 43/12* | (2006.01) | |
| *A61L 26/00* | (2006.01) | |
| *A61K 31/198* | (2006.01) | |
| *A61K 31/7008* | (2006.01) | |
| *A61K 31/717* | (2006.01) | |
| *A61K 31/726* | (2006.01) | |
| *A61K 31/737* | (2006.01) | |
| *A61K 33/30* | (2006.01) | |
| *A61K 33/38* | (2006.01) | |
| *A61K 35/644* | (2015.01) | |
| *A61K 36/06* | (2006.01) | |
| *F04B 15/02* | (2006.01) | |
| *F04B 51/00* | (2006.01) | |
| *A61Q 19/00* | (2006.01) | |
| *A61P 17/02* | (2006.01) | |
| *A61K 9/00* | (2006.01) | |
| *A61K 9/06* | (2006.01) | |

(52) U.S. Cl.
CPC ............ *F04B 51/00* (2013.01); *A61K 8/042* (2013.01); *A61K 8/65* (2013.01); *A61K 31/198* (2013.01); *A61K 31/7008* (2013.01); *A61K 31/717* (2013.01); *A61K 31/726* (2013.01); *A61K 31/737* (2013.01); *A61K 33/30* (2013.01); *A61K 33/38* (2013.01); *A61K 35/644* (2013.01); *A61K 36/06* (2013.01); *A61K 38/014* (2013.01); *A61K 38/018* (2013.01); *A61K 45/06* (2013.01); *A61L 26/008* (2013.01); *A61L 26/0033* (2013.01); *A61P 17/02* (2018.01); *A61Q 19/00* (2013.01); *C07K 14/78* (2013.01); *F04B 15/02* (2013.01); *F04B 43/12* (2013.01); *A61K 9/0014* (2013.01); *A61K 9/06* (2013.01); *F04B 2205/11* (2013.01)

(58) Field of Classification Search
CPC .............. A61K 2300/00; A61K 31/198; A61K 31/7008; A61K 31/717; A61K 31/726; A61K 31/737; A61K 33/30; A61K 33/38; A61K 35/644; A61K 36/06; A61K 38/018; A61K 38/014; A61K 45/06; A61K 8/042; A61K 8/65; A61K 9/0014; A61K 9/06; C07K 14/78; C07K 1/12; C07K 1/34; F04B 43/12; F04B 51/00; F04B 15/02; F04B 2205/11; A61L 26/0033; A61L 26/008; A61P 17/02; A61Q 19/00

See application file for complete search history.

(56) References Cited

U.S. PATENT DOCUMENTS

| | | | |
|---|---|---|---|
| 3,578,876 A | 5/1971 | Stratienko | |
| 3,831,907 A | 8/1974 | Claes | |
| 4,426,443 A | 1/1984 | Shank | |
| 4,837,024 A * | 6/1989 | Michaeli | A61K 38/39 424/422 |
| 5,304,355 A | 4/1994 | Yant et al. | |
| 5,447,369 A | 9/1995 | Boxall | |
| 6,136,341 A | 10/2000 | Petito | |
| 6,533,449 B1 | 3/2003 | Auad | |
| 8,118,191 B2 | 2/2012 | Belongia et al. | |

FOREIGN PATENT DOCUMENTS

| | | |
|---|---|---|
| CN | 205099606 U | 3/2016 |
| JP | 3-216182 A | 9/1991 |

* cited by examiner

*Primary Examiner* — Aaron J Kosar
(74) *Attorney, Agent, or Firm* — Richard C. Litman; Nath, Goldberg & Meyer

(57) ABSTRACT

The method of making a hydrolyzed collagen gel is a manufacturing method for producing a hydrolyzed collagen gel to be used as a topical wound treatment. A first volume of purified water is initially heated to a temperature ranging from about 71° C. to about 77° C., and a hydrolyzed type I collagen powder is then mixed into the heated purified water to form a first mixture. An additive is mixed into the first mixture to form a second mixture, where the additive may be native collagen, at least one amino acid, least one therapeutic agent, gelatin, whey, hydrolyzed whey, polysulfated glycosaminoglycan, a glucosamine salt, glutamine, glycosaminoclycans, zinc, silver oxide alginates, cellulose, honey, mushroom extract and combinations thereof. A second volume of purified water is then added to the second mixture to form the hydrolyzed collagen gel product. Mixing is performed as a continuous, recirculating, temperature-monitored and temperature-maintained process.

19 Claims, 2 Drawing Sheets

METHOD OF MAKING A HYDROLYZED COLLAGEN GEL

BACKGROUND OF THE INVENTION

1. Field of the Invention

The present invention relates to collagen-based wound treatments, and particularly to a method of making a hydrolyzed collagen gel for usage as a topical wound treatment.

2. Description of the Related Art

Open wounds in the skin are a potential gateway for infectious or contaminating material to enter the body. The skin is a protective barrier to external contaminants. When the skin is damaged with an open breach, these contaminants are free to enter the body. Once inside the body, these contaminants may have effects of varying degrees, but almost always become more difficult to treat and, consequently, slow the process of healing the original wound. In order to fight infection, wound management traditionally involves an initial cleansing of the affected area to remove any contaminants, such as dirt, clothing particles, foreign agents or other debris. Damaged tissue and foreign materials are removed when necessary, and antiseptic agents are applied to sterilize the injured area.

Sterile dressings are often applied, and are periodically changed to keep the injured area as clean and sterile as possible. Complex biological mechanisms occur during the healing process, such as chemical signals attracting fibroblast cells to the wound site, which ultimately generate connective structures, mainly of collagen. Endothelial cells generate new blood capillaries that nurture the new growth. Cell growth continues until the open wound is filled by forming permanent new tissue.

Hydrolyzed collagen has been found to facilitate the healing of damaged tissues, as well as promoting tissue and cell growth, protecting cells and tissues, and reducing scar tissue. It would obviously be desirable to be able to efficiently produce a hydrolyzed collagen product which is suitable for use as a topical treatment for wound healing. Thus, a method of making a hydrolyzed collagen gel solving the aforementioned problems is desired.

SUMMARY OF THE INVENTION

The method of making a hydrolyzed collagen gel includes a manufacturing method for producing a hydrolyzed collagen gel, which may be used as a topical wound treatment or the like. It should be noted that the hydrolyzed collagen gel may be used as a medical grade topical wound treatment, may be used for cosmetic purposes, or may be used for any other suitable purposes. A first volume of purified water is initially heated to a temperature between 71° C. and 77° C., and a hydrolyzed type I collagen powder is then mixed into the heated purified water to form a first mixture. The hydrolyzed type I collagen powder is a source of proteinaceous amino acids. An additive is mixed into the first mixture to form a second mixture. The additive may include native collagen, further sources of amino acids, and/or at least one other therapeutic agent. For example, further sources of amino acids may include gelatin, whey, or hydrolyzed whey, and the therapeutic agent may be a polysulfated glycosaminoglycan, a glucosamine salt, glutamine, glycosaminoclycans, zinc, silver oxide alginates, cellulose, mushroom extract and/or honey or mixtures thereof. A second volume of purified water is then added to the second mixture to form the hydrolyzed collagen gel product. Mixing is performed as a continuous, recirculating, temperature-monitored and temperature-maintained process.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
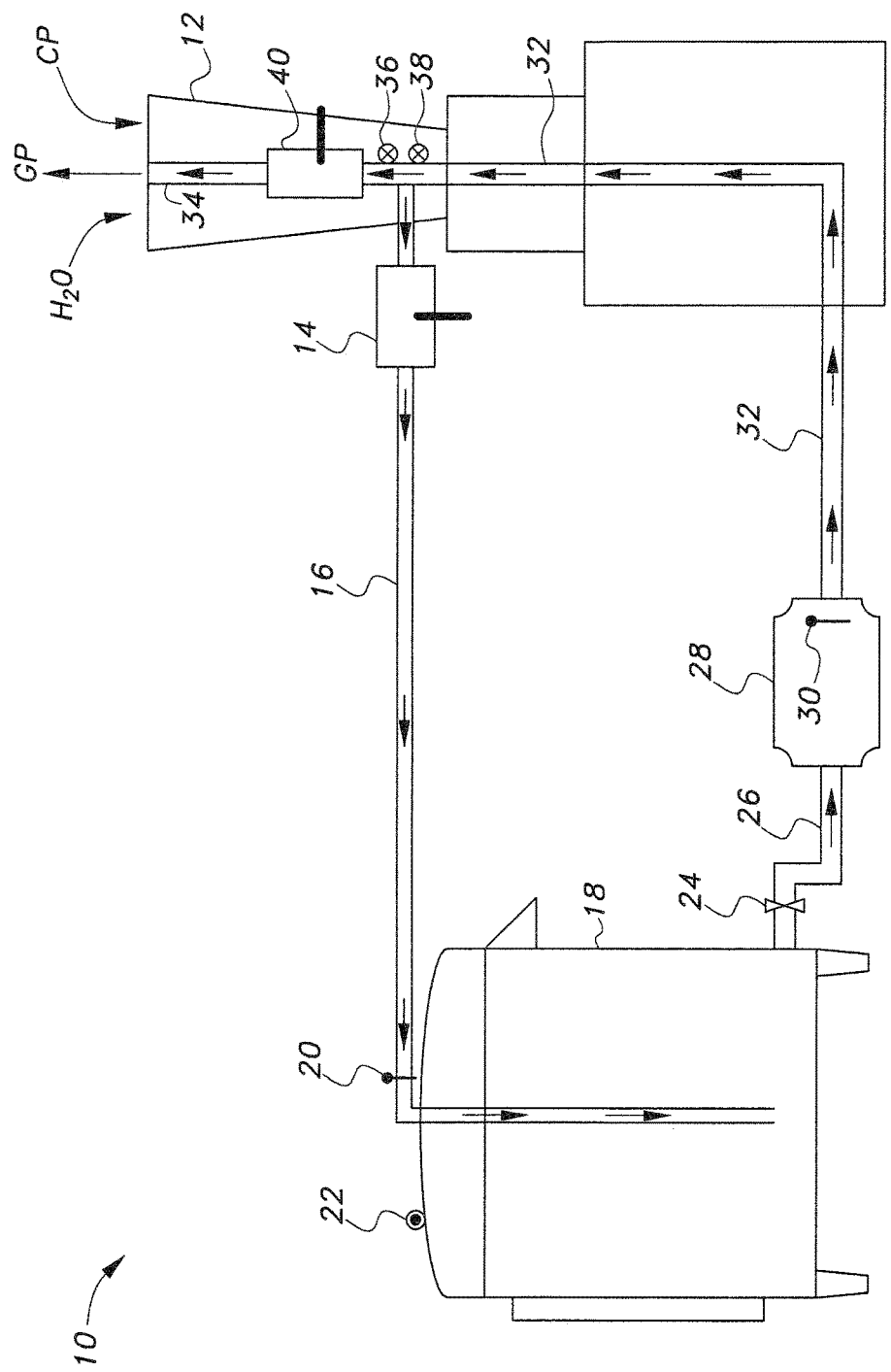
FIG. 1 diagrammatically illustrates a system for implementing a method of making a hydrolyzed collagen gel according to the present invention.

The method of making a hydrolyzed collagen gel includes a manufacturing method for producing a hydrolyzed collagen gel, which may be used as a topical wound treatment or the like. It should be noted that the hydrolyzed collagen gel may be used as a medical grade topical wound treatment, may be used for cosmetic purposes, or may be used for any other suitable purposes. A first volume of purified water is initially heated to a temperature ranging from about 71° C. to about 77° C., with a preferred temperature of approximately 74° C. A hydrolyzed type I collagen powder, having an average molecular weight of less than 10,000 Da, is then mixed into the heated purified water to form a first mixture. The hydrolyzed collagen gel can be prepared using exemplary system 10, diagrammatically illustrated in FIG. 1. As shown in FIG. 1, the purified water ($H_2O$) and the hydrolyzed type I collagen powder (CP) are input to hopper 12 of system 10. The purified water and the hydrolyzed type I collagen powder are fed into a combination mixing and heating tank 18, as will be described in greater detail below, via flow through line 16. Flow through line 16, which is a recirculating return line, as will be described in greater detail below, may be controlled by a ball valve 14 or the like.

The hydrolyzed type I collagen powder preferably has an average molecular weight ranging from about 2,000 Da to about 4,000 Da, and more preferably has an average molecular weight ranging from about 2,500 Da to about 2,800 Da. The hydrolyzed type I collagen powder may be any suitable hydrolyzed type I collagen powder, such as that described in U.S. Pat. No. 6,136,341, which is hereby incorporated by reference in its entirety. It should be noted that temperature range between 71° C. and 77° C., with a preferred temperature of approximately 74° C., is important, since exceeding this range may result in protein collapse and integrity loss of the resultant gel product, and temperatures below this range may result in particle dispersion and incomplete chemical dissolution. As shown in FIG. 1, system 10 includes a thermocouple sensor 20 or the like, positioned in the upper portion of return line 16, to ensure the target temperature is maintained, and the combination mixing and heating tank 18 includes a pressure gauge 22, ensuring that both temperature and pressure are maintained at this stage of the process.

The hydrolyzed type I collagen powder is preferably mixed into the heated purified water in a conventional propeller mixer with side sweeps, represented in FIG. 1 as combination mixing and heating tank 18, to form a first mixture. The propeller speed preferably begins at about 240 rpm and is raised, as the hydrolyzed type I collagen powder is added, to a speed of about 1460 rpm. Similarly, the side sweep frequency is preferably raised throughout the mixing, beginning at about 25 Hz (15 rpm) and rising to about 35 Hz (22 rpm). The first mixture is preferably mixed for a period of time ranging from about 20 minutes to about 30 minutes. Throughout mixing of the first mixture, the temperature is preferably maintained at a temperature ranging from about 71° C. to about 77° C. As noted above, the target temperature is continuously monitored by thermocouple sensor 20 to ensure the temperature is maintained.

It is important to note that mixing and processing preferably takes place in stainless steel mixers, lines, etc. or the like, since the end product, as well as the pre-products for the end gel product, are adhesive in nature. The maintenance of the materials in the desired temperature range, as described above, further prevents the materials from hardening and solidifying during the manufacturing process. Preferably, the propeller mixer or kettle 18 is of the conventional type using dual propellers, with both 3" and 5" propellers used. Such propeller mixers are well known in the art, with the 3" diameter propeller, for example, being positioned within a top portion of the mixer, and with the 5" diameter propeller, for example, being positioned about ¾ from the top of the mixer (i.e., at 75% of the depth of the mixture in the heated mixer/kettle). Such propeller mixers with side swept agitation are well known in the art, and it should be understood that any suitable type of mixer may be used. For example, the mixer may be a 40 gallon, model TA steam jacket kettle, manufactured by Groen Process Equipment of Cary, Ill.

Additionally, in order to prevent solidifying and hardening of the mixtures, processing preferably includes recirculation of the mixtures, as shown in FIG. 1. Once the mixed material exits combination mixing and heating tank 18 via outlet valve 24, the mixture passes through line 26 to peristaltic pump 28. The peristaltic pump 28 is indexed through partial revolution to deliver smaller amounts of the mixture in order to prevent solidification and hardening, as noted above. A second thermocouple sensor 30 or the like is preferably attached to the pump wall, or is adjacent thereto, in order to maintain the proper temperature of the mixture in the target temperature range. Preferably, the temperature sensors 20, 30 are immersed in the mixture during the mixing process. The peristaltic pump 28 preferably operates at a speed less than 1800 rpm in order to maintain temperatures in the mixer 18, as well as maintain control over the fluid mixing.

The peristaltic pump 28 drives the mixture through line 32 to recirculate back into line 16, as shown in FIG. 1, maintaining the mixing process through a temperature-monitored, temperature-maintained, recirculated process.

In addition to the purified water and the hydrolyzed type I collagen powder making up the first mixture, an additive is mixed into the first mixture to form a second mixture. The hydrolyzed type I collagen powder is a source of proteinaceous amino acids. The additive may include native collagen, further sources of amino acids, and/or at least one other therapeutic agent. For example, further sources of amino acids may include gelatin, whey, or hydrolyzed whey, and the therapeutic agent may be a polysulfated glycosaminoglycan, a glucosamine salt, glutamine, glycosaminoclycans, zinc, silver oxide alginates, cellulose, mushroom extract and/or honey or mixtures thereof. The second mixture is preferably mixed in the propeller mixer 18 for a period of time ranging from about 8 minutes to about 12 minutes, with a propeller speed of approximately 800 rpm, and a side sweep frequency ranging between 25 Hz (15 rpm) and 35 Hz (22 rpm). It should be understood that the above exemplary values for speed, temperature and pressure may vary dependent upon the choice of the additive. For example, honey, which is relatively viscous, will require the usage of a special pump, as well as having separate temperature and pressure ranges as it is fed into the solution.

A second volume of purified water is then added to the second mixture to form the hydrolyzed collagen gel product. During heating, some of the initial purified water is lost to evaporation, thus the second volume of purified water is added to make up for the lost water. Preferably, the end gel product is about 67.00 wt % hydrolyzed type I collagen and about 32.71 wt % water. The additive forms the remaining approximate 0.29 wt % of the final product. The mixing with the second volume of purified water is preferably performed at a temperature ranging from about 71° C. to about 77° C. for approximately 10 minutes in order to ensure complete incorporation of the additional purified water.

The gel product may be additionally filtered through a 100 μm filter, for example, and then dispensed into an electric kettle. The kettle is used to maintain the filtered product at the desired temperature range between 71° C. and 77° C. It is important to note that as the final gel product is dispensed, the product must be continuously mixed while maintaining the temperature range between 71° C. and 77° C. As the product is dispensed, mixing speeds may be adjusted accordingly to prevent product aeration. Propeller mixing must stop completely after this dispensing, as the product level will no longer support it. Only side sweep agitation may be used for the continuous mixing throughout. In FIG. 1, as shown, the hydrolyzed collagen gel product (GP) may be drawn out of the system via line 34, which is preferably monitored by a flow meter 36 and a pressure gauge 38, with output being controlled by a ball valve 40 or the like.

Figure 2:
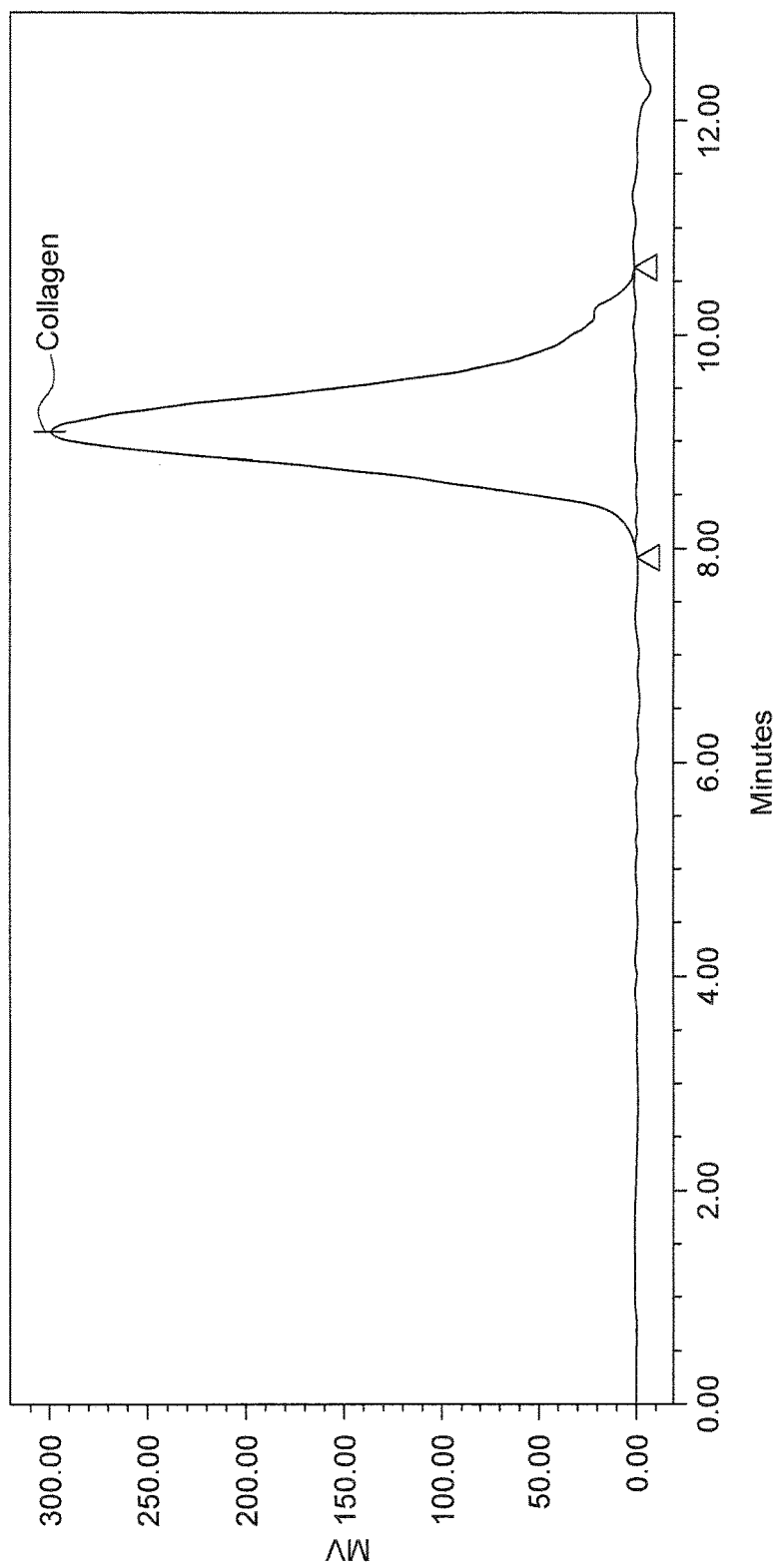
FIG. 2 is a graph showing aqueous size exclusion chromatography with refractive index detection results of a pure collagen assay of a hydrolyzed collagen gel sample made by the method of making a hydrolyzed collagen gel according to the present invention.

A hydrolyzed collagen gel product was prepared as described herein. In order to confirm the collagen content of the hydrolyzed collagen gel product, a sample was assayed by aqueous size exclusion chromatography with refractive index detection. FIG. 2 shows the results of the assay for pure collagen with a 13.0 minute run time. The analysis yielded 14.90 mg/mL pure collagen in the sample analyzed, corresponding to 37.25 wt % of pure collagen detected.

It is to be understood that the present invention is not limited to the embodiments described above, but encompasses any and all embodiments within the scope of the following claims.

I claim:

1. A method of making a hydrolyzed collagen gel, comprising the steps of:
heating a first volume of water to a temperature ranging from about 71° C. to about 77° C.;
mixing a hydrolyzed type I collagen powder into the heated water to form a first mixture;
mixing an additive into the first mixture to form a second mixture, wherein the additive is selected from the group consisting of native collagen, at least one amino acid, least one therapeutic agent, gelatin, whey, hydrolyzed whey, polysulfated glycosaminoglycan, a glucosamine salt, glutamine, glycosaminoclycans, zinc, silver oxide alginates, cellulose, honey, mushroom extract and combinations thereof; and
adding a second volume of water to the second mixture to form a hydrolyzed collagen gel.

2. The method of making a hydrolyzed collagen gel as recited in claim 1, wherein the step of heating the water comprises heating the water to a temperature of 74° C.

3. The method of making a hydrolyzed collagen gel as recited in claim 1, wherein the step of mixing the hydrolyzed type I collagen powder into the heated water comprises mixing the hydrolyzed type I collagen powder and the heated water in a propeller mixer with side sweeps.

4. The method of making a hydrolyzed collagen gel as recited in claim 3, wherein the step of mixing the hydrolyzed type I collagen powder into the heated water comprises mixing the hydrolyzed type I collagen powder and the heated water in the propeller mixer at a propeller speed between 240 rpm and 1460 rpm.

5. The method of making a hydrolyzed collagen gel as recited in claim 4, wherein the step of mixing the hydrolyzed type I collagen powder into the heated water comprises mixing the hydrolyzed type I collagen powder and the heated water in the propeller mixer with a side sweep frequency between 25 Hz and 35 Hz.

6. The method of making a hydrolyzed collagen gel as recited in claim 5, wherein the step of mixing the hydrolyzed type I collagen powder into the heated water comprises mixing the hydrolyzed type I collagen powder and the heated water in the propeller mixer for a period of time ranging from about 20 minutes to about 30 minutes.

7. The method of making a hydrolyzed collagen gel as recited in claim 1, wherein the hydrolyzed type I collagen powder has an average molecular weight ranging from about 1,000 Da to about 10,000 Da.

8. The method of making a hydrolyzed collagen gel as recited in claim 7, wherein the hydrolyzed type I collagen powder has an average molecular weight ranging from about 2,000 Da to about 4,000 Da.

9. The method of making a hydrolyzed collagen gel as recited in claim 8, wherein the hydrolyzed type I collagen powder has an average molecular weight ranging from about 2,500 Da to about 2,800 Da.

10. The method of making a hydrolyzed collagen gel as recited in claim 1, wherein the step of mixing the additive into the first mixture comprises mixing the additive and the first mixture in the propeller mixer for a period of time ranging from about 8 minutes to about 12 minutes.

11. The method of making a hydrolyzed collagen gel as recited in claim 10, wherein the step of mixing the additive into the first mixture comprises mixing the additive and the first mixture in the propeller mixer with a propeller speed of 800 rpm.

12. The method of making a hydrolyzed collagen gel as recited in claim 11, wherein the step of mixing the additive into the first mixture comprises mixing the additive and the first mixture in the propeller mixer with a side sweep frequency ranging from about 25 Hz to about 35 Hz.

13. The method of making a hydrolyzed collagen gel as recited in claim 1, wherein the step of adding the second volume of water to the second mixture to form the hydrolyzed collagen gel comprises adding the second volume of water to the second mixture to form the hydrolyzed collagen gel such that a concentration of the hydrolyzed type I collagen in the hydrolyzed collagen gel is about 67.00 wt %.

14. The method of making a hydrolyzed collagen gel as recited in claim 13, wherein the step of adding the second volume of water to the second mixture to form the hydrolyzed collagen gel comprises adding the second volume of water to the second mixture to form the hydrolyzed collagen gel such that a concentration of the additive in the hydrolyzed collagen gel is 0.29 wt %.

15. A method of making a hydrolyzed collagen gel, comprising the steps of:
    heating a first volume of water to a temperature ranging from about 71° C. to about 77° C.;
    mixing a hydrolyzed type I collagen powder into the heated water to form a first mixture;
    mixing an additive into the first mixture to form a second mixture, wherein the additive is selected from the group consisting of native collagen, at least one amino acid, least one therapeutic agent, gelatin, whey, hydrolyzed whey, polysulfated glycosaminoglycan, a glucosamine salt, glutamine, glycosaminoclycans, zinc, silver oxide alginates, cellulose, honey, mushroom extract and combinations thereof; and
    adding a second volume of water to the second mixture to form a hydrolyzed collagen gel, wherein a concentration of the hydrolyzed type I collagen in the hydrolyzed collagen gel is about 67.00 wt %, a concentration of the additive in the hydrolyzed collagen gel is about 0.29 wt %, and a concentration of the water in the hydrolyzed collagen gel is about 32.71 wt %.

16. The method of making a hydrolyzed collagen gel as recited in claim 15, wherein the step of mixing the hydrolyzed type I collagen powder into the heated water comprises mixing the hydrolyzed type I collagen powder and the heated water in a propeller mixer with side sweeps.

17. The method of making a hydrolyzed collagen gel as recited in claim 16, wherein the step of mixing the hydrolyzed type I collagen powder into the heated water comprises mixing the hydrolyzed type I collagen powder and the heated water in the propeller mixer at a propeller speed ranging from about 240 rpm to about 1460 rpm.

18. The method of making a hydrolyzed collagen gel as recited in claim 17, wherein the step of mixing the hydrolyzed type I collagen powder into the heated water comprises mixing the hydrolyzed type I collagen powder and the heated water in the propeller mixer with a side sweep frequency ranging from about 25 Hz to about 35 Hz.

19. The method of making a hydrolyzed collagen gel as recited in claim 18, wherein the step of mixing the hydrolyzed type I collagen powder into the heated water comprises mixing the hydrolyzed type I collagen powder and the heated water in the propeller mixer for a time period ranging from about 20 minutes to about 30 minutes, and the step of mixing the additive into the first mixture comprises mixing the additive and the first mixture in the propeller mixer with a propeller speed of about 800 rpm and with a side sweep frequency ranging from about 25 Hz to about 35 Hz.

* * * * *